United States Patent [19]

Masuda et al.

[11] Patent Number: 4,861,552
[45] Date of Patent: * Aug. 29, 1989

[54] BIOLOGICAL REACTION LAYER AND ITS PREPARATION

[75] Inventors: Nobuhito Masuda; Shigeru Nagatomo; Hajime Makiuchi; Yukio Yasuda, all of Asaka, Japan

[73] Assignee: Fuji Photo Film Co., Ltd., Kanagawa, Japan

[ * ] Notice: The portion of the term of this patent subsequent to Sep. 18, 2001 has been disclaimed.

[21] Appl. No.: 851,878

[22] Filed: Apr. 11, 1986

Related U.S. Application Data

[63] Continuation of Ser. No. 557,660, Dec. 2, 1983, abandoned.

[30] Foreign Application Priority Data

Dec. 3, 1982 [JP]   Japan .................................. 57-211382

[51] Int. Cl.$^4$ ..................... C12Q 1/00; G01N 33/52; G01N 33/543; G01N 33/548
[52] U.S. Cl. ......................... 422/56; 435/4; 435/805; 436/500; 436/501; 436/518; 436/524; 436/528; 436/530; 436/810
[58] Field of Search ....................... 427/2; 422/56, 57; 435/805, 4; 436/500, 501, 518, 528, 530, 535, 808, 810

[56] References Cited

U.S. PATENT DOCUMENTS

| | | | |
|---|---|---|---|
| 4,472,498 | 9/1984 | Masuda | 435/805 |
| 4,587,102 | 5/1986 | Nagatomo et al. | 436/810 X |
| 4,657,739 | 4/1987 | Yasuda et al. | 436/810 X |

*Primary Examiner*—Johnnie R. Brown
*Assistant Examiner*—Jeremy M. Jay
*Attorney, Agent, or Firm*—Jules E. Goldberg

[57] ABSTRACT

A biological reaction layer of a dry analytical element in the form of a composite porous layer in which a particulate material carrying a biologically active material fixed thereon is dispersed in a fibrous porous matrix, characterized in that the dry weight ratio of said particulate material to said fibrous material contained in said composite porous layer ranges from 1:20 to 1:0.3 and said particulate material is contained therein in the range of 1 to 60 g/m$^2$.

4 Claims, No Drawings

BIOLOGICAL REACTION LAYER AND ITS PREPARATION

This is a continuation of application Ser. No. 557,660 filed 12-2, 1983, abandoned.

BACKGROUND OF THE INVENTION

1. Field of the Invention

This invention relates to a biological reaction layer and a process for the preparation of the same.

2. Description of Prior Arts

A number of analytical systems for detecting and quantitatively analyzing trace components in a liquid sample, for example, biochemically active components and other organism-originating components contained in a biological fluid such as body fluid, using an analytical element (dry analytical element) constituted in a form of a layer (or sheet) have been well known. The analytical element is generally employed in such a manner that a material chemically or physically reactive to a substance to be analyzed (analyte) upon contact therebetween incorporated previously into the analytical element is brought into contact with the analyte in a liquid sample introduced into the element in an analysis operation to undergo a certain reaction within a biological reaction layer, and the amount of the reaction product or the unreacted substance is measured by spectrophotometry or fluorometry, or by radioisotope to determine the amount of the analyte.

Since the above-mentioned analytical method utilizing an analytical element is relatively simple in the analytical operation, the method has been used for many purposes, for example, in immunoassay utilizing antigen-antibody reaction, analysis of enzyme or substrate utilizing enzymic reaction or the like. However, the so advantageously simple method using analytical element has a drawback such as insufficient analytical sensitivity.

For instance, the above-mentioned drawback is particulary serious in the immunoassay. More in detail, in order to obtain analytical results with high sensitivity, it is required in the immunoassay that a liquid sample of a sufficient volume is introduced in an analytical element within a short time, and then the liquid sample must be retained for a sufficient period of time to complete the antigen-antibody reaction. However, the liquid sample of sufficient volume per unit area is hardly retained in a conventional analytical element, and hence the sufficient sensitivity can not be obtained. A number of analytical elements have been proposed to eliminate such disadvantagous feature in the immunoassay but these elements have eliminated the above-mentioned disadvantage only insufficiently.

Furthermore, the above-mentioned disadvantage is also true to a certain extent in other analytical methods using analytical elements in which enzymic reactions or other various reactions participates.

SUMMARY OF THE INVENTION

A principal object of the present invention is to provide a biological reaction layer that is employable as a part or the whole of an analytical element to eliminate or reduce the above-mentioned disadvantage.

There is provided by the present invention a biological reaction layer or a dry analytical element in the form of a composite porous layer in which a particulate material carrying a biologically active material fixed thereon is dispersed in a fibrous porous matrix, characterized in that the dry weight ratio of said particulate material to said fibrous material contained in said composite porous layer ranges from 1:20 to 1:0.3 and said particulate material is contained therein in the range of 1 to 60 g/m$^2$.

DETAILED DESCRIPTION OF THE INVENTION

A biological reaction layer of the invention comprises, in a basic structure, a composite porous layer in which a particulate material carrying a biologically active material fixed thereon is dispersed in a fibrous porous matrix. More in detail, the biological reaction layer of the invention is constituted basically of a combination of a matrix of fibrous material aggregated to form a porous structure and a particulate material distributed uniformly in spaces defined by the matrix of fibrous material. To the particulate material is fixed a biologically active material, that is, a material which is actively maintained thereon to participate in the aimed biological reaction.

There is no specific limitation on the fibrous material employable in the invention, as far as it is essentially inert to the liquid sample and analyte introduced into the analytical element. Examples of the employable fibrous material include inorganic fibers such as glass fibers and asbestos, natural organic fibers such as cotton, hemp, pulp and silk, semi-synthetic or synthetic fibers such as viscose rayon, cuprammonium rayon, cellulose acetate, partially formalized polyvinyl alcohol, polyethylene, polypropylene, polyvinyl chloride, polystyrene and polyesters (e.g., polyethylene terephthalate, etc.).

The thickness of the fibrous material preferably ranges from 0.1 to 5 μm, and the length from 500 to 4000 μm.

There is no specific limitation on the particulate material employable in the invention, as far as it is essentially inert to the liquid sample and analyte introduced into the analytical element. Examples of the employable particulate material are non-fibrous materials, for instance, polysaccharides such as agar, agarose, sepharose, sephadex and dextran; polyacrylamides and latex formed by the polymerization (or copolymerization) of polymerizable ethylenic monomers; and cellulose powder. Among these materials, non-fibrous materials such as, agar, agarose and sepharose are preferably employed because the use of these materials can increase the amount of a liquid sample retainable therein per thickness of the biological reaction layer.

The particulate material preferably is in the form of sticks, in which the ratio of the minor axis (width or thickness) to the major axis (length) ranges from 1:1 to 1:20 . However, there is no specific limitation on the shape of the particulate material. For instance, a material of optional shape, such as a sphere, circular cone, pyramid, prism or cylinder including modifications or combinations of these shapes, can be employed. A limp fibrous material with a long fiber length is not preferable as the particulate material, because such a fibrous material is liable to be entangled with the above-mentioned fibrous material to resulting in a non-uniform biological reaction layer.

Furthermore, the mean diameter of the above-mentioned particulate material ranges preferably from 10 to 200 μm.

In the case that an antigen-antibody reaction is utilized for the quantitative analysis, the biologically active material fixed on the particulate material keeping the activity thereof can be an antibody of the analyte, such as, immunoglobulin, etc. Further, the biologically active material can be an antigen (including hapten and analogues thereof) in the case that the analyte is an antibody. In the case that an enzyme-substrate reaction is utilized for the analysis, glucose oxidase or horseradish peroxidase, or their combination can be employed for the quantitative detection of glucose, and a substrate having a dye-forming group such as, starch carrying a dye or coupler can be employed for detection of amylase. In these cases, a certain compound may be required to provide a detectable signal (for instance, o-phenylenediamine is required in the above-mentioned glucose detection, and a coupler is required in the amylase detection).

The procedure to fix the biologically active material on the particulate material keeping the activity thereof can be performed according to known methods or similar methods. A fluorescent label or radioactive label may be provided to the active material so as to make the active material itself, decomposition products thereof, or combination products of the active material and the analyte detectable. The procedure for providing these labels to the active material have been heretofore known, and accordingly the detailed description of the procedure is omitted.

The reaction applicable to the fixation of the biologically active material and to the labeling procedure is described in detail in the following literatures.

TEXT FOR BIOCHEMICAL EXPERIMENTS, VOL. 1 (Chemistry of Proteins), VOL. 2 (Chemistry of Nucleic Acids), VOL. 3 (Chemistry of Fats), and VOL. 4 (Chemistry of Saccharides) (compiled by The Society of Biochemistry, Japan, published by Tokyo Kagaku Dozin, 1977)

METHOD FOR SYNTHESIS OF PEPTIDES (by Izumiya et al., published by Maruzen, 1975)

ENZYMEIMMUNO-ASSAY (by Kiyoshi Miyai, Rinsho Kensa Vol. 22, No. 11, 1978, extra issue)

METHOD FOR ENZYMEIMMUNOASSAY (compiled by Ishikawa et al., published by Igaku Shoin, 1978)

The label may be attached to the analyte if required. If a competitive reaction between an antigen and its labeled antigen against their common antibody is to be performed in the biological reaction layer of the invention, an antibody can be beforehand incorporated into the reaction layer for serving as the biologically active substance. In the reaction layer, the antibody is then brought into contact with the analyte (antigen) and a labeled substance such as, a labeled analyte or a labeled homologue to perform the competitive reaction.

The biological reaction layer of the invention is in a form of composite porous layer having such advantageous features that a liquid samplke containing an analyte can enter and diffuse easily and the liquid sample can be retained for a fairly long time within the layer. In order to attain these advantages, it is required that the dry weight ratio of said particulate material to the fibrous material contained in said composite porous material ranges from 1:20 to 1:0.3 and said particulate material is contained in the amount of 1 to 60 g/m$^2$.

If one or both of these two conditions, that is, the dry weight ratio of said particulate material to said fibrous material and the content of the particulate material in the composite porous layer, deviate from the above-mentioned respective ranges, one or both of the entering and diffusion of the liquid sample and the retention of the liquid sample in the biological reaction layer will be insufficient, and the inventive improvement cannot be attained.

The thickness of the composite porous layer of the invention, i.e. the biological reaction layer, preferably ranges from 100 to 2000 μm, more preferably from 200 to 1000 μm.

The biological reaction layer of the invention constituted as described above is prepared preferably by the following process.

A process for the preparation of a biological reaction layer which comprises:

adjusting the thickness of a wet mixture layer comprising a particulate material carrying a biologically active material fixed thereon, fibrous material, and a liquid dispersing medium in which the dry weight ratio of said particulate material to said fibrous material ranges from 1:20 to 1:0.3 and said particulate material is contained in an amount of 1 to 60 g/m$^2$, by means of a member or members having a predetermined clearance, and drying said layer with substantially no change in the predetermined thickness to produce a composite porous layer.

The above-mentioned process is performed, for example, by a procedure comprising the steps of: preparing a slurry in which a particulate material carrying a biologically active material fixed thereon and fibrous material are dispersed in a liquid dispersing medium (for example, water or a mixture of water and a water-miscible organic solvent) in a ratio within the above-mentioned range; forming a layer of a wet mixture containing said particulate material in an amount of 1 to 60 g/m$^2$ by processing the slurry through a conventional paper making procedure; adjusting the thickness of the layer using a member or members having a predetermined clearance (the surface of the member or members preferably is smooth); and drying the layer with substantially no change in the predetermined thickness (the drying procedure is preferably carried out at a low temperature, and the freeze-drying is preferably employed).

In the preparation of the above-mentioned slurry, various agents which are conventionally used in paper making process, such as, a dispersant, a thickner, and a preservative can be employed, provided that the function of the resulting biological reaction layer is not damaged by these agents. There is no specific limitation on the procedure for preparing the slurry. For example, various methods using conventional mixers such as homogenizer and a ball mill or using an apparatus generally employable for preparing a paper slurry, such as, a beater can be used.

There is no specific limitation on the procedure for preparing the wet mixture layer (voluminous layer). For example, various methods using conventional fourdrinier machines and cylinder machines or using a static paper making screen through which the aqueous dispersion is filtered can be used.

The wet mixture layer containing the liquid dispersing medium as well as the particulate material and the fibrous material in which the weight ration (former: latter, dry basis) is in the range of 1:20 to 1:0.3 and the particulate material is contained in an amount of 1 to 60 g/m$^2$ is then adjusted in the thickness. The procedure for adjusting the thickness of the layer is performed by means of a member or members having a predetermined clearance. Various procedures can be employed to adjust the thickness. Examples of the procedure include a procedure comprising compressing the layer between two flat plates to reach the predetermined thickness and a procedure comprising causing the layer to pass between rolls having a predetermined clearance (slit). The thickness of the layer is preferably adjusted to reach within a range of 100 to 2000 μm, and then the adjusted layer is dried with substantially no change in the thickness.

In order to attain the above-mentioned purpose, the layer is preferably dried at a relatively low temperature or more preferably freeze-dried. The drying at a lower temperature and particularly freeze-drying are preferable also because the biologically active material contained in the layer prepared as above can be dried with substantially no deterioration of the activity thereof.

Alternatively, the adjustment of thickness of the layer prepared as above can be done in other stages. For example, the biological reaction layer of the invention can be prepared by adjusting the thickness of the layer with a member or members having a predetermined clearance (the surface of the member or members preferably is smooth) after drying the layer. The above-mentioned adjusting procedure employing the flat plates and rolls can be applied to this case, and the thickness of the dried layer can be adjusted in the same manner using these devices.

The biological reaction layer of the invention has a smooth surface and increased porosity, and a liquid sample applied onto the surface by a procedure, such as, spotting is distributed uniformly inside of the layer within a short time. The porous structure comprising fibrous material of the biological reaction layer of the invention, which is different from the conventional sheet-shaped biological reaction layer, has high porosity, and the biological reaction layer of the invention can retain a great amount of a liquid sample during the process of introduction and distribution of the liquid sample. Therefore, the biological reaction layer of the invention eliminates the aforementioned problems attached to the prior art, that is, both the rapid distribution of the liquid and the retention of a great amount of the liquid for a longer time can be accomplished by the invention.

For the above-mentioned reasons, the biological reaction layer of the invention is of value as a reaction layer of an analytical element for the immunoassay in which both the rapid distribution of the liquid and the retention of a great amount of the liquid for a longer time are particularly desired.

The biological reaction layer of the invention is as such employable as an analytical element, but it is preferably employed in the form of multilayer analytical element comprising a laminated structure of a plurality of layers so as to increase the accuracy of the analysis.

As far as the immunoassay is concerned, a multilayer analytical element of the following structure can be employed: a layer structure comprising, in order:

(a) a biological reaction layer according to the invention in which a particulate material carrying a certain amount of a protein specifically bindable to an analyte fixed thereon is dispersed uniformly in a porous structure composed of glass fibers in a certain ratio; and (b) a porous spreading sheet (layer) comprising a certain amount of a fluorescent-labeled analyte or analogue thereof within a matrix of a fibous material or non-fibrous material.

In the case that the biological reaction layer of the invention is used in a multilayer analytical element utilizing the enzymic reaction, the structure described below can be employed:

a structure comprising a spreading layer disclosed in Japanese Patent Provisional Publications Nos. 49(1974)-53888, 55(1980)-90859, 55(1980)-164356, etc., a biological reaction layer (enzyme or substrate carrying a dye-forming group or a coupler group fixed thereon), and a color-forming reaction layer, or a structure comprising a light-shielding layer in addition to the above-mentioned structure.

The multilayer analytical element comprising the above-mentioned structures are known as analytical element for various purposes and structures. Accordingly, the biological reaction layer of the invention can be likewise formed in optional structures and employed for various purposes.

Examples of the invention are described in the following, but the examples by no means, limit the invention.

EXAMPLES

I-1

Preparation of agarose carrying anti-thyroxine (anti-$T_4$) antibody thereon 0.2 ml. of saturated aqueous ammonium sulfate solution was added to 0.3 ml. of anti-thyroxine antiserum, and mixed under ice-cooling. The resulting mixture was allowed to stand for 10 min to give a precipitate. This was then subjected to centrifugal separation (3000 r.p.m., 10 min.) to give an IgG fraction of the anti-$T_4$ antibody.

15 g. of CNBr-activated Sepharose 4B (produced by Pharmacia Fine Chemicals) was swollen with 100 ml. of water, and washed on a glass filter with 2 l. of $10^{-3}N$ hydrochloric acid.

The anti-$T_4$ antibody IgG fraction was dissolved in 30 ml. of 0.1M bicarbonate buffer solution (pH 8.5, 0.5M sodium chloride was contained), and the fraction was added to the washed CNBr-activated Sepharose 4B. The resulting mixture was kept under stirring at 4° C. for 16 hours to perform reaction. After the reaction was terminated, the reaction solvent was removed on a glass filter. Subsequently, 50 ml. of 1M ethanolamine (adjusted to pH 8 to 8.5 with hydrochloric acid) was added, and the mixture was kept at 4° C. for 2 to 5 hours for performing the reaction. The reaction mixture was washed on a glass filter three times alternately with 0.1M acetic acid buffer solution (pH 4.0, 1M sodium chloride was contained) and 0.1M boric acid buffer solution (pH 8.0, 1M sodium chloride was contained). After the washing was complete, the product was preserved in 0.1M glycine buffer solution (pH 9.0, 0.1M sodium chloride and 0.1% sodium azide were contained) at 4° C.

I-2

Preparation of reaction layer for measurement of thyroxine 2 g. of a glass fiber filter paper GA-100 (manufactured by Toyo Filter Paper Co. Ltd., Japan) was cut into approx. 3 mm×3 mm pieces, and dispersed in 400 ml. of water with a homogenizer (manufactured by Nippon Seiki Co., Ltd., Japan) at 15000 r.p.m. for 10 min. The dispersion was sifted alternately with a 2 mm×2 mm stainless mesh and a 1 mm×1 mm stainless mesh, and the thus obtained glass fibers of the 1 mm×1 mm mesh over were dispersed in 500 ml. of 0.1M glycine buffer solution (pH 9.0, 0.5M sodium chloride was contained). A certain volume of this dispersion was taken out and filtered on a filter manufactured by Millipore Corporation to collect the length-adjusted glass fibers on the filter. The residual water was dropped and dried, and the weight was measured to determine the glass fiber concentration in the dispersion (mg/ml).

A certain volume of the glass fiber dispersion was so taken out that 30 mg of glass fibers was contained in the taken-out dispersion. To this dispersion was added 0.45 ml. of the anti-$T_4$ antibody-fixed Sepharose 4B prepared in the example I-1. The resulting mixture was spread in a filtering device manufactured by Millipore Corporation (filter: HAWP, pore size 0.45 μm diameter, 47 mm) to produce a voluminous paper. The thus produced voluminous paper was transferred together with the filter employed onto a glass plate, and sandwiched between two glass plates through spacers with a thickness of 500 μm to adjust the thickness. The paper was then frozen, the glass plates were removed, and the paper was freeze-dried.

I-3

Evaluation of reaction layer for measurement of anti-thyroxine

Ten pieces of 8 mm×8 mm reaction layers were cut from one reaction layer (diameter: 36 mm) prepared in the example I-2, and these were named the Sample A group. A reaction layer was prepared in the same manner as in the example I-2 except for replacing the anti-$T_4$ antibody-fixed Sepharose 4B with a simple Sepharose 4B, and 8 mm×8 mm cut pieces were prepared in the same manner, and these were named the Sample B group.

$^{125}$I-labeled $T_4$ prepared by the New England Nuclear Corporation was diluted with 0.1M barbital buffer solution (pH 8.6, 0.1% BSA: bovine serum albumin was contained) to prepare the solution of 15,000 c.p.m. per 100 μl.

The pieces of Sample A group and sample B group were placed separately on a Teflon sheet. 100 μl of the diluted $^{125}$I-labeled $T_4$ solution was poured on each piece, and allowed to undergo reaction at 4° C. for 2 hours. Then, each piece was put on a micro filter to remove the liquid, and washed with 100 μl of 0.1M barbital buffer solution (pH 8.6) three times. After washing was complete, the piece was transferred into a small test tube, and the radioactivity was measured.

As the result of the measurement, the sample A group gave value of 11,552±232 c.p.m., and the Sample B group gave value of 293±50 c.p.m. These values indicated that the reaction layers prepared in the example I-b 2, namely, the Sample A group, were provided with highly uniform reactivity.

Ten 8 mm×8 mm pieces were cut from five reaction layers prepared in the example I-2 respectively. Three pieces were selected respectively from each layer, and totally fifteen pieces were named the Sample C group.

On the Sample C group, the reactivity to the $^{125}$I-labeled $T_4$ was examined under the same conditions as above, and values of 11,703±278 c.p.m. were obtained. From this result, it was confirmed that the procedure of the Sample I-2 exhibited excellent reproducibility.

We claim:

1. A composite porous layer for a dry analytical element comprising a particulate material carrying an immunologically active material fixed thereon which is dispersed in a fibrous porous matrix, wherein a dry weight ratio of said particulate material to said fibrous material ranges from 1:20 to 1:0.3 and said particulate material is contained in the range of 1 to 60 g/m$^2$.

2. The composite porous layer as claimed in claim 1 wherein said particulate material has a mean diameter in the range of 10 to 200 μm.

3. The composite porous layer as claimed in claim 1 wherein said fibrous material has a thickness and a length in the range of 0.1 to 5 μm and 500 to 4,000 μm, respectively.

4. The composite porous layer as claimed in claim 1 wherein said composite porous layer has a thickness in the range of 100 to 2,000 μm.

* * * * *